United States Patent
Narayanan et al.

(10) Patent No.: US 9,560,847 B2
(45) Date of Patent: Feb. 7, 2017

(54) STABLE MATRIX EMULSION CONCENTRATES AND STABLE AQUEOUS AND/OR ORGANIC SOLVENT COMPOSITIONS CONTAINING BIOCIDES

(75) Inventors: Kolazi S. Narayanan, Wayne, NJ (US); Xianbin Liu, Basking Ridge, NJ (US); Karen Winkowski, Springfield, NJ (US); Jayanti Patel, Elmwood Park, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 2336 days.

(21) Appl. No.: 10/990,995

(22) Filed: Nov. 17, 2004

(65) Prior Publication Data
US 2006/0105007 A1 May 18, 2006

(51) Int. Cl.
*A01N 25/04* (2006.01)
*A01N 47/12* (2006.01)

(52) U.S. Cl.
CPC ............... *A01N 25/04* (2013.01); *A01N 47/12* (2013.01)

(58) Field of Classification Search
CPC ...... A01N 47/12; A01N 25/04; A01N 43/653; A01N 53/00; A01N 25/22
See application file for complete search history.

(56) References Cited

U.S. PATENT DOCUMENTS

| 5,013,748 | A | * | 5/1991 | Radtke et al. | 514/383 |
| 5,731,264 | A | * | 3/1998 | Narayanan et al. | 504/363 |
| 5,827,522 | A | * | 10/1998 | Nowak | 424/405 |
| 6,045,816 | A | * | 4/2000 | Narayanan et al. | 424/405 |
| 6,187,715 | B1 | * | 2/2001 | Narayanan et al. | 504/118 |
| 2002/0168417 | A1 | * | 11/2002 | Blease et al. | 424/600 |

FOREIGN PATENT DOCUMENTS

EP   1300448 A2 *  4/2003   ............... C09D 5/02

OTHER PUBLICATIONS

Alkalmus RS-710 product data sheet, 1 page.*

* cited by examiner

*Primary Examiner* — Kyle Purdy
(74) *Attorney, Agent, or Firm* — Thompson Hine LLP; William J. Davis

(57) ABSTRACT

A stable matrix emulsion concentrate of a biocide, e.g. 3-iodopropynyl-2-butyl carbamate (IPBC) and/or a triazole fungicide, and stable aqueous and/or organic solvent formulations thereof, i.e. dilutable in water and/or an organic solvent are provided, which are particularly useful for treating wood products to provide protection against microorganisms and insects.

10 Claims, No Drawings

STABLE MATRIX EMULSION CONCENTRATES AND STABLE AQUEOUS AND/OR ORGANIC SOLVENT COMPOSITIONS CONTAINING BIOCIDES

BACKGROUND OF THE INVENTION

1. Field of the Invention

This invention relates to biocidal compositions, and, more particularly, to IPBC (3-iodopropynyl)-2-butyl carbamate and/or triazole fungicide, containing compositions in the form of a stable microemulsion concentrate and an aqueous or organic dilution composition suitable for treating wood products to protect them against attack by fungus and other diseases.

2. Description of the Prior Art

Biocides are essential components of cosmetic formulations and paint compositions. However, for treating wood products no current formulations of biocides, e.g. IPBC or propiconazole (a triazole) are available because the biocide separates from aqueous dilution solutions (see U.S. Pat. No. 5,827,522).

Accordingly, it is an object of this invention to provide a stable matrix emulsion concentrate in which the biocide is dissolved at high loadings, and which remains stable when diluted in a suitable organic solvent, and also is dilutable with water to form a stable aqueous microemulsion without separation at room temperature for an extended period of time. The resultant product is an aqueous microemulsion composition suitable for wood treatment in which the biocides therein provide effective protection for wood against microorganisms and insects.

SUMMARY OF THE INVENTION

What is described herein is a stable microemulsion concentrate including, by weight,
(a) 1-40% of a biocide, e.g. (3-iodopropynyl)-2-butyl carbamate (IPBC) and/or a triazole, e.g. (propiconazole),
(b) a matrix of
  (i) 0-30% of a $C_1$-$C_4$ N-alkyl pyrrolidone,
  (ii) 0.5-30% of a $C_8$-$C_{14}$ N-alkyl pyrrolidone,
  (iii) 4-85% of castor oil ethoxylate,
  (iv) 0.5-20% of an ethylene oxide/propylene oxide copolymer, and
  (v) 0.05-5% of an ethoxylated phosphate ester.

Preferably the stable microemulsion concentrate of the invention also includes (c) an organic solvent as diluent, e.g. a hydrocarbon, preferably an aromatic petroleum distillate, esters, ketones, ethers, vegetable oils, and alcohols, e.g. trimethyl benzene, propylene carbonate or isopropyl alcohol and mixtures thereof, which are present in an amount of about 10-60% by weight of the diluted concentrate.

Preferably, (a) is present in an amount of about 15-30%, and (b) (ii) of about 10-20%.

Suitably (b) (iii) contains 30 EO units; and (b) (v) 9-10 EO units.

The invention also includes stable microemulsion compositions including the microemulsion concentrate described above and water and/or organic solvent of dilution, optionally then including a water soluble biocide, e.g. a quat. Accordingly, stable aqueous microemulsion compositions are provided upon dilution of the concentrate with water, e.g. 1 part of emulsion concentrate to 20-1000 parts of water, to produce biocidal compositions in a usable biocidal range, e.g. 100-5000 ppm biocide.

The invention will be described in more detail with the following examples.

Suitable candidates for the biocidal material are IPBC; benzisothiazolones; propiconazole (CAS-60207-90-1); permethryn (CAS-52645-53-1), [(3-(2,2-dichloroethenyl)-2,2-dimethyl-cyclopropane carboxylic acid (3-phenoxyphenyl)-methyl ester)]; deltamethrin (CAS-52918-63-5)[(3-(2,2-dibromoethenyl)-2,2-dimethyl-cyclopropane carboxylic acid cyano (3-phenoxyphenyl) methyl ester]; cypermethrin (CAS-52315-07-8)[(3-(2,2-dichloroethenyl)-2,2-dimethyl-cyclopropane carboxylic acid cyano (3-phenoxyphenyl) methyl ester)]; chlorpyriphos (CAS-2921-88-2)[(Allethrin) (0,0-diethyl O-(3,5,6-Trichloro-2-pyridinyl)phosphorothiate)]; tebuconazole (CAS107534-96-3); 8-hydroxyquinoline (CAS-148-24-3); 2-(hydroxymethylamino)ethanol (CAS-65184-12-5); iodopropynyl cyclohexyl carbamate; Irgarol (n-cyclopropynyl-$N^1$-(1,1-dimethylethyl)-6-(methylthio)-1, 3,5-triazine-2,4-diamine); 2,4-dichloro phenoxyacetic acid, butyl ester; 2,4,5-trichlorophenoxy acetic acid, ethyl ester; 2,4 dichlorbutyric acid, ethyl ester; Chlordane; piperonyl butoxide; bromoxynil (3,5-dibromo-4-hydroxy benzonitrile ester of n-octanoic acid); Thanite®; isobornylthiocyanoacetate; iodo propargyl succinate; terbutryn (CAS-886-50-0) [(2-tert-butylamino-4-ethylamino-6-methylthio-1,3,5-triazine)]; 5-chloro-2-methyl-4-isothiazolin-3-one, 2-methyl-4-isothiazolin-3-one; 1,4-dichloro-2,5-dimethoxy benzene (Chloroneb); orthophenylphenol; ~(RS)-3-allyl-2-methyl-4 okocyclopent-2-enyl (IRS) Cu; trans chrysan the math (IUPAC); azaconazole; cyperconazole; Amical (diiodomethyl-p-tolyl sulfone); IF-1000 (iodopropynyl phenylether); Cyfluthrin (CAS-68359-37-5); beta cyfluthrin (CFAS-68359-37-5); lambda-cyhalothrin (CAS-91465-08-6); cyhexatin (CAS-13121-70-5); cyphenothrin (CAS-39515-40-7); endosulfan (CAS-115-29-7); (1,4,5,6,7,7-hexachloro 8,9,10-trinorborn-5-en-2,3-ylene bismethylene) sulfide (IUPAC); fenitrothion (CAS-122-14-5).

The water miscible biocidal concentrate compositions of the present invention have potential application in a variety of circumstances including, but not limited to disinfectants, sanitizers, cleaners, deodorizers, liquid and powder soaps, skin removers, oil and grease removers, food processing chemicals, wood preservation, polymer latices, paint lazures, stains, mildewcides, hospital and medical antiseptics, medical devices, metal working fluids, cooling water, air washers, petroleum protection, paper treatment, pulp and paper slurries, paper mill slimicides, petroleum products, adhesives, textiles, pigment slurries, latexes, leather and hide treatment, petroleum fuel, jet fuel, laundry sanitizers, agricultural formulations, inks, mining, non-woven fabrics, petroleum storage, rubber, sugar processing, tobacco, swimming pools, photographic rinses, cosmetics, toiletries, pharmaceuticals, chemical toiletries, household laundry products, diesel fuel additives, waxes and polishes, oil field applications, and many other applications where water and organic materials come in contact under conditions which allow the growth of undesired microorganisms.

The following examples are presented to illustrate and explain the invention. Unless otherwise indicated, all references to parts and percentages are based on weight.

EXAMPLES

A. General Method of Preparation of Matrix and Biocide-Containing Emulsion Concentrates of Invention The matrix compositions shown in the following Examples were prepared by weighing in appropriate quantities of the ingredients to make up 100 g samples in 2, 4 or 8 ounce stoppered bottle. The contents were dissolved using a rotary shaker over a period of 16 hours. All compositions were homogeneous at room temperature. Appropriate quantities of the active biocide ingredient, e.g. IPBC, was weighted into the matrix to prepare 100 g of the emulsion concentrates containing the biocide. The biocide was dissolved in the matrix by shaking the mixture in a rotary shaker over a period of 16 hours.

1. Preparation of Matrix

Example 1

A 100 g matrix was prepared by dissolving the following ingredients in a 4-ounce stoppered bottle. N-methylpyrrolidone, 21.5 g; N-octyl pyrrolidone, 9.7 g; castor oil ethoxylate (30 EO), 58.6 g; EO/PO copolymer, 8.7 g; and branched ethoxylated phosphate ester (9-10 EO), 1.5 g.

Example 2

A 100 g matrix composition was prepared by dissolving the following ingredients in a 4-ounce stoppered bottle. N-octyl pyrrolidone, 12.5 g; castor oil ethoxylate (30 EO), 74.5 g; EO/PO copolymer, 11.0 g; and branched ethoxylated phosphate ester (9-10 EO), 2.0 g.

Example 3

80 g of Matrix 2 was mixed with 20 g of a petroleum distillate (Exxon aromatic oil 150).

Example 4

85 g of Matrix 2 was mixed with 15 g of a petroleum distillate (Exxon aromatic oil 150).

Example 5

78.5 g of Matrix 1 was mixed with 21.5 g of propylene carbonate.

Example 6

50 g of Matrix 2 was mixed with 50 g of propylene carbonate.

Example 7

80 g of Matrix 2 was mixed with 20 g of propylene carbonate.

2. Preparation of Biocide Concentrates

Example 8

20 g IPBC was dissolved in 80 g of the composition of Example 3 to produce a 20% IPBC emulsion concentrate.

Example 8A 20 g propiconazole was dissolved in 80 g of the composition of Example 3 to produce a 20% concentrate.

Example 9

20 g of IPBC was dissolved in 80 g of the composition of Example 4 to produce 20% concentrate.

Example 9A 20 g propiconazole was dissolved in 80 g of the composition of Example 4 to produce a 20% concentrate.

Example 10

20 g of IPBC was dissolved in 80 g of the composition of Example 5 to produce a 20% concentrate.

Example 10A 20 g propiconazole was dissolved in 80 g of the composition of Example 5 to produce a 20% concentrate.

Example 11

20 g of IPBC was dissolved in 80 g of the composition of Example 6 to produce a 20% concentrate.

Example 11A 20 g propiconazole was dissolved in 80 g of the composition of Example 6 to produce a 20% concentrate.

Example 12

20 g of IPBC was dissolved in 80 g of the composition of Example 7 to produce a 20% concentrate.

Example 12A 20 g propiconazole was dissolved in 80 g of the composition of Example 7 to produce a 20% concentrate.

Example 13

20 g of IPBC was dissolved in 80 g of composition shown in Example 2 to produce a 20% concentrate.

Example 13A 20 g propiconazole was dissolved in 80 g of composition shown in Example 2 to produce a 20% concentrate.

Example 14

30 g of IPBC was dissolved in 70 g of the composition of Example 4 to produce a 30% concentrate.

Example 14A 20 g propiconazole was dissolved in 70 g of composition shown in Example 4 to produce a 20% concentrate.

Example 15

10 g IPBC and 10 g propiconazole were dissolved in 80 g of composition shown in Example 4 to produce a concentrate containing mixed fungicides at 10% IPBC and 10% propiconazole.

Example 16

20 g of IPBC was dissolved in a mixture containing 40 g of composition of Example 4 and 40 g of didecyl dimethyl ammonium chloride (DDAC quat, 80%).

Stability of Concentrates shown in Examples 8 through 16

All concentrates were clear, homogeneous solutions at ambient conditions and at 50° C. and at 0° C. when stored for three weeks. The samples passed the standard freeze/thaw cycle test of three times of alternate storage at 50° C. and 0° C. through room temperature for 24 hours at each temperature without any separation. (See procedure shown in U.S. Pat. No. 6,045,816).

Stability on Dilution

The concentrates shown in Examples 8 through 15 were diluted with deionized water as well as 1000 ppm WHO hard water at the rates: 1/10, 1/100, and 1/1000 and any separation was noted by visual observation as a function of time during storage at room temperature (22° C.-25° C.). The results are summarized in the Table below:

TABLE

|  | 1/10 | 1/100 | 1/1000 |
| --- | --- | --- | --- |
| Example 8 Dilution In Water, Time, T (days) | | | |
| T = 0 D | no ppt, creamy at bottom | cloudy, no ppt | cloudy, no ppt |
| T = 0 D to 1 D | no ppt, creamy at bottom | cloudy, no ppts | cloudy, no ppt |
| T = 1 D to 3 D | no ppt, creamy at bottom | cloudy, no ppt | cloudy, no ppt |
| T = 3 D to 7 D | cloudy, ppt | cloudy, ppt | cloudy, no ppt |
| T = 7 D to 15 D | cloudy, ppt | cloudy, ppt | cloudy, ppt |
| T = 15 D to 30 D | cloudy, ppt | cloudy, ppt | cloudy, ppt |
| Example 9 | | | |
| T = 0 D | clear to opaque, no ppt | clear to opaque, no ppt | clear - slightly cloudy, no ppt |
| T = 0 D to 2 D | clear - slightly cloudy, slight ppt | clear - slightly cloudy, no ppt | clear - slightly cloudy |
| T = 2 D to 3 D | clear - slightly cloudy, ppt | clear - slightly cloudy, no ppt | clear - slightly cloudy |
| T = 3 D to 7 D | clear - slightly cloudy, ppt | clear - slightly cloudy, ppt | clear - slightly cloudy |
| T = 7 D to 15 D | clear - slightly cloudy, ppt | clear - slightly cloudy, ppt | clear - slightly cloudy |
| Example 10 In Water | | | |
| T = 0 D | no ppt, creamy white | no ppt, creamy white | no ppt, dark opaque |
| T = 0 D to 1 D | ppt, creamy white | ppt, creamy white | no ppt, dark opaque |
| T = 1 D to 3 D | ppt, creamy white | ppt, creamy white | no ppt, dark opaque |
| T = 3 D to 7 D | ppt, creamy white | ppt, creamy white | no ppt, dark opaque |
| T = 7 D to 15 D | ppt, creamy white | ppt, creamy white | no ppt, dark opaque |
| T = 15 D to 30 D | ppt, creamy white | ppt, creamy white | no ppt, dark opaque |
| Example 11 | | | |
| T = 0 D | dark opaque, no ppt | dark opaque, no ppt | clear white |
| T = 0 D to 2 D | clear - slightly cloudy, no ppt | dark opaque, ppt | clear - slightly cloudy, no ppt |
| T = 2 D to 3 D | clear - slightly cloudy, ppt | clear - slightly cloudy, ppt | clear - slightly cloudy, no ppt |
| T = 3 D to 7 D | clear - slightly cloudy, ppt | clear - slightly cloudy, ppt | clear - slightly cloudy, no ppt |
| T = 7 D to 15 D | clear - slightly cloudy, ppt | clear - slightly cloudy, ppt | clear - slightly cloudy, no ppt |
| Example 12 | | | |
| T = 0 D | dark opaque, no ppt | dark opaque, no ppt | clear white |
| T = 0 D to 2 D | creamy white, slight ppt | creamy white, slight ppt | clear - slightly cloudy, no ppt |
| T = 2 D to 3 D | creamy white, ppt | creamy white, ppt | clear - slightly cloudy, no ppt |
| T = 3 D to 15 D | creamy white, ppt | creamy white, ppt | clear - slightly cloudy, no ppt |
| Example 13 In water | | | |
| T = 0 D | milky white, no ppt | dark opaque, no ppt | clear - slightly cloudy, no ppt |
| T = 0 D to 3 D | milky white, ppt | dark opaque, ppt | clear - slightly cloudy, no ppt |
| T = 3 D to 5 D | milky white, ppt | milky white, ppt | clear - slightly cloudy, no ppt |
| T = 5 D to 15 D | milky white, ppt | milky white, ppt | clear - slightly cloudy, no ppt |
| Example 14 | | | |
| T = 0 D | no ppt, creamy at bottom | cloudy, no ppt | cloudy, no ppt |
| T = 0 D to 1 D | no ppt, creamy at bottom | cloudy, no ppt | cloudy, no ppt |
| T = 1 D to 3 D | no ppt, creamy at bottom | cloudy, no ppt | cloudy, no ppt |
| T = 3 D to 7 D | no ppt, creamy at bottom | cloudy, no ppt | cloudy, no ppt |
| T = 7 D to 15 D | cloudy, ppt | cloudy, ppt | cloudy, ppt |
| T = 15 D to 30 D | cloudy, ppt | cloudy, ppt | cloudy, ppt |

The diluted compositions from Example 9 and 16 without separation at 1/1000 dilution during storage for 4 months.

Compositions 8A, 9A, 1A, 11A, 12A, 13A, 14A containing propiconazole behaved similar to the corresponding compositions containing IPBC on dilution.

Additional Physical Stability Tests

| Formulation | Freeze-thaw stability (3 cycles) | Dilution stability at 1.0% in water after 3 days |
| --- | --- | --- |
| Example 9 | Stable | Stable |
| Example 16 | Stable | Stable |
| 20% IPBC in Castor oil ethoxylated - Control* | Stable | Unstable, crystal formation |

*U.S. Pat. No. 5,827,522

Biological Testing Results*

Southern yellow pine wood blocks (12×24×1 cm$^3$) were dipped in each of the following IPBC containing formulation at 1.0% for 3 seconds and then air dried for 24 hours. The dried blocks were hanged in the environmental chamber with mixture of microorganisms at 32° C. for a period of time to let microorganisms grow. The test results are as follows:

| Formulation | Readings at 3 weeks | Readings at 6 weeks | Readings at 12 weeks |
| --- | --- | --- | --- |
| Water | 2 | 8 | 10 |
| Example 9 | 0 | 2 | 5 |
| Example 16 | 0 | 0 | 3 |

* The readings are based on the following scale: 0 stands for no growth; 10 stands for 80% of coverage by microorganisms.

While the invention has been described with particular reference to certain embodiments thereof, it will be understood that changes and modifications may be made which are within the skill of the art. Accordingly, it is intended to be bound only by the following claims, in which:

What is claimed is:

1. A stable microemulsion concentrate comprising, by weight,
   (a) 1-40% of a biocide selected from iodopropargyl butyl carbamate, or the combination of iodopropargyl butyl carbamate and propiconazole,
   (b) a matrix of:
      (i) 0-30% of a $C_1$-$C_4$ N-alkyl pyrrolidone,
      (ii) 0.5-30% of a $C_8$-$C_{14}$ N-alkyl pyrrolidone,
      (iii) 4-85% of castor oil ethoxylate,
      (iv) 0.5-20% of an ethylene oxide/propylene oxide copolymer, and
      (v) 0.05-5% of an ethoxylated phosphate ester, and
   (c) an organic solvent as diluent wherein said organic solvent is propylene carbonate.

2. A stable microemulsion concentrate according to claim 1 wherein (c) is present in an amount of 10-60% by weight of the diluted concentrate.

3. A stable microemulsion concentrate according to claim 2 wherein (a) is about 15-30%.

4. A stable microemulsion concentrate according to claim 1 wherein (b) (ii) is about 10-20%.

5. A stable microemulsion concentrate according to claim 1 wherein (b) (iii) contains 30 EO units; and (b) (v) contains 9-10 EO units.

6. A concentrate according to claim 1 which includes a quat.

7. A stable microemulsion composition including the microemulsion concentrate of claim 1 and water and/or an organic solvent of dilution.

8. A stable aqueous microemulsion composition according to claim 7 which is diluted with water and/or organic solvent at a concentration of 1 part of emulsion concentrate to 20-1000 parts of water and/or organic solvent of dilution.

9. A composition of claim 7 which includes about 100-5000 ppm of biocide.

10. A composition according to claim 7 which also includes a quat.

* * * * *